United States Patent [19]
Leost

[11] Patent Number: 5,610,326
[45] Date of Patent: Mar. 11, 1997

[54] NON-DESTRUCTIVE PROCESS FOR CHARACTERIZING THE SURFACE CONDITION OF A PART

[75] Inventor: Daniel L. L. Leost, Soisy sur Seine, France

[73] Assignee: Societe Nationale d'Etude et de Construction de Moteurs d'Aviation "Snecma", Paris, France

[21] Appl. No.: 495,395

[22] Filed: Jun. 28, 1995

[30] Foreign Application Priority Data

Jun. 30, 1994 [FR] France ............... 94 08058

[51] Int. Cl.⁶ .................................................. G01B 5/28
[52] U.S. Cl. ............................................. 73/105; 73/104
[58] Field of Search ............................... 73/105, 104

[56] References Cited

U.S. PATENT DOCUMENTS

| | | | |
|---|---|---|---|
| 3,913,393 | 10/1975 | Facy | 73/105 |
| 4,043,187 | 8/1977 | Tomomatsu | 73/105 |
| 4,198,362 | 4/1980 | Ticker et al. | 73/105 X |
| 4,303,608 | 12/1981 | Ticker et al. | 73/105 X |
| 4,346,588 | 8/1982 | Tuttle | 73/105 |

FOREIGN PATENT DOCUMENTS

| | | |
|---|---|---|
| 853567 | 3/1940 | France . |
| 2472182 | 6/1981 | France . |
| 59-079832 | 5/1984 | Japan . |
| 02170010 | 6/1990 | Japan . |
| 03221831 | 9/1991 | Japan . |
| 05045266 | 2/1993 | Japan . |

*Primary Examiner*—Thomas P. Noland
*Attorney, Agent, or Firm*—Oblon, Spivak, McClelland, Maier & Neustadt, P.C.

[57] ABSTRACT

A process for checking the surface condition of a part, particularly in areas which are difficult to access, comprises making a rough preliminary imprint of the surface using an elastomeric material of medium precision in paste form and allowing the material to harden so that the preliminary imprint forms a supporting mold, casting a high precision elastomeric material, preferably in silicone based material, into the supporting mold and applying it to the surface to form an accurate imprint which is allowed to harden and, after removal, is inspected to determine the surface condition.

5 Claims, 3 Drawing Sheets

NON-DESTRUCTIVE PROCESS FOR CHARACTERIZING THE SURFACE CONDITION OF A PART

BACKGROUND OF THE INVENTION

1. Field of the invention

The invention relates to a non-destructive process for characterizing the surface condition of a part in order to check its roughness and reveal any defects. The process may be applied in particular to the examination of shot-blasted surfaces and is especially suitable for inspection of areas with difficult access.

Shot blasting processes consist of bombarding the surface of a part with steel, glass or ceramic balls. These processes are used particularly in applications seeking to obtain surface compression prestressing in order to improve the operating performance of the parts by increasing the fatigue resistance or the corrosion resistance under stress. As the complexity of the shape of the part to be treated increases, it becomes more difficult to obtain the required degree of application of the shot to the part. A good quality assurance of parts is required more and more, and it is therefore necessary to ensure that the degree of shot blasting is sufficient and that the shot blasting extends without interruption over the whole of the treated surface.

2. Summary of the Prior Art

There are a variety of methods enabling the surface condition of a part to be checked. In particular it is known to check the surface condition of parts by the inspection of imprints. Each imprint is obtained by placing on the surface to be examined a sheet of plastic film, for example of cellulose acetate, soaked in acetone so as to soften it in order for it to adopt faithfully the shape of the part. After hardening, the imprinted sheet is removed and may be viewed using a binocular magnifier, an optical microscope or a scanning electron microscope. This technique is currently used for examining shot-blasted, sanded, ground or machined surfaces, as it makes it possible at the same time to validate parts, store the surface conditions through the imprints, and carry out topographic appraisals. However, the technique is difficult to carry out and is inapplicable in areas which are difficult to access. Moreover, precautions have to be taken to prevent the imprints exhibiting serious defects, such as air inclusions. Furthermore, the technique is difficult to apply when the ambient temperature is high because of the rapid evaporation of acetone.

It is also known to check the surface condition of a part by taking dimensional readings which enable a measurement of roughness to be obtained. In particular, in the field of metrology dimensional readings are taken from imprints made using self-polymerizing methyl methacrylate based fluid resins belonging to the acrylic resin family. However, this type of resin cannot be used for checking the condition of surfaces in inaccessible areas as it is too fluid and very adherent after hardening. Moreover, the accuracy of detail obtained with this type of resin is insufficient and, generally, it contains numerous air inclusions.

The surface condition resulting from shot-blasting may also be checked from technological test pieces representative of the parts subjected to the blast of shot. However, making test pieces is a constraint in terms of cost and does not supply an accurate indication of the real surface condition of the parts.

SUMMARY OF THE INVENTION

It is an object of the invention to overcome the drawbacks of the known methods by providing a method of checking the surface condition resulting from the shot blasting of a mechanical part which is easy to implement, does not require the use of complex and costly equipment, makes it possible to obtain accurate reliable data, and is capable of being used in areas with difficult access.

Another object of the invention is to provide a checking process which facilitates the validation of mechanical parts, can be used for taking highly precise topographic surveys, and makes it possible to take dimensional readings characteristics of the roughness, with a high degree of accuracy.

Accordingly, the invention provides a non-destructive process for characterizing the surface condition of a part, including the steps of:

applying a first elastomeric material in paste form to the surface to be checked and allowing said first elastomeric material to harden to obtain a supporting mold bearing a preliminary imprint of said surface;

casting a second elastomeric material in paste form into said supporting mold to form an impression element, said second elastomeric material having a mean consistency permitting the reproduction of detail with an accuracy of the order of a few tenths of a micron;

applying said impression element to said surface to be checked so as to obtain a final imprint of said surface in said impression element;

holding said impression element in place on said surface for sufficient time for said element to harden; and, removing said hardened element with said final imprint from said surface.

The process thus involves making a highly accurate imprint of the area to be examined using an elastomeric material in paste form, preferably a silicone-based material having natural nonadherence, such as, for example, the pastes used in dentistry, and removing and examining the imprint after it has hardened. A variety of different examinations are possible. In particular, the imprint may be studied with a binocular magnifying glass, and/or photographed with an optical or scanning electron microscope. The imprint may also be used for roughness measurements taken, for example, using a laser profilometer. The imprint is generally free from air inclusions.

For inspections with a binocular magnifier, it is preferable first to metallize the imprint so as to increase the optical contrast. When a scanning electron microscope or an optical microscope is used, metallization is imperative, as it enables the surface to be made conductive and reflective.

The imprints made in accordance with the invention from silicone based elastomeric materials can be easily stored, as they are very strong and afford excellent resistance to natural aging. Their reproduction accuracy is comparable to that obtained from an imprint made with a sheet of plastics film. Also, they are not harmful in any way to parts which include titanium, as their chlorine content is low.

Other features and advantages of the invention will become apparent from the following description of the preferred embodiments, given by way of example, with reference to the attached drawings.

DESCRIPTION OF THE PREFERRED EMBODIMENTS

Figure 1:
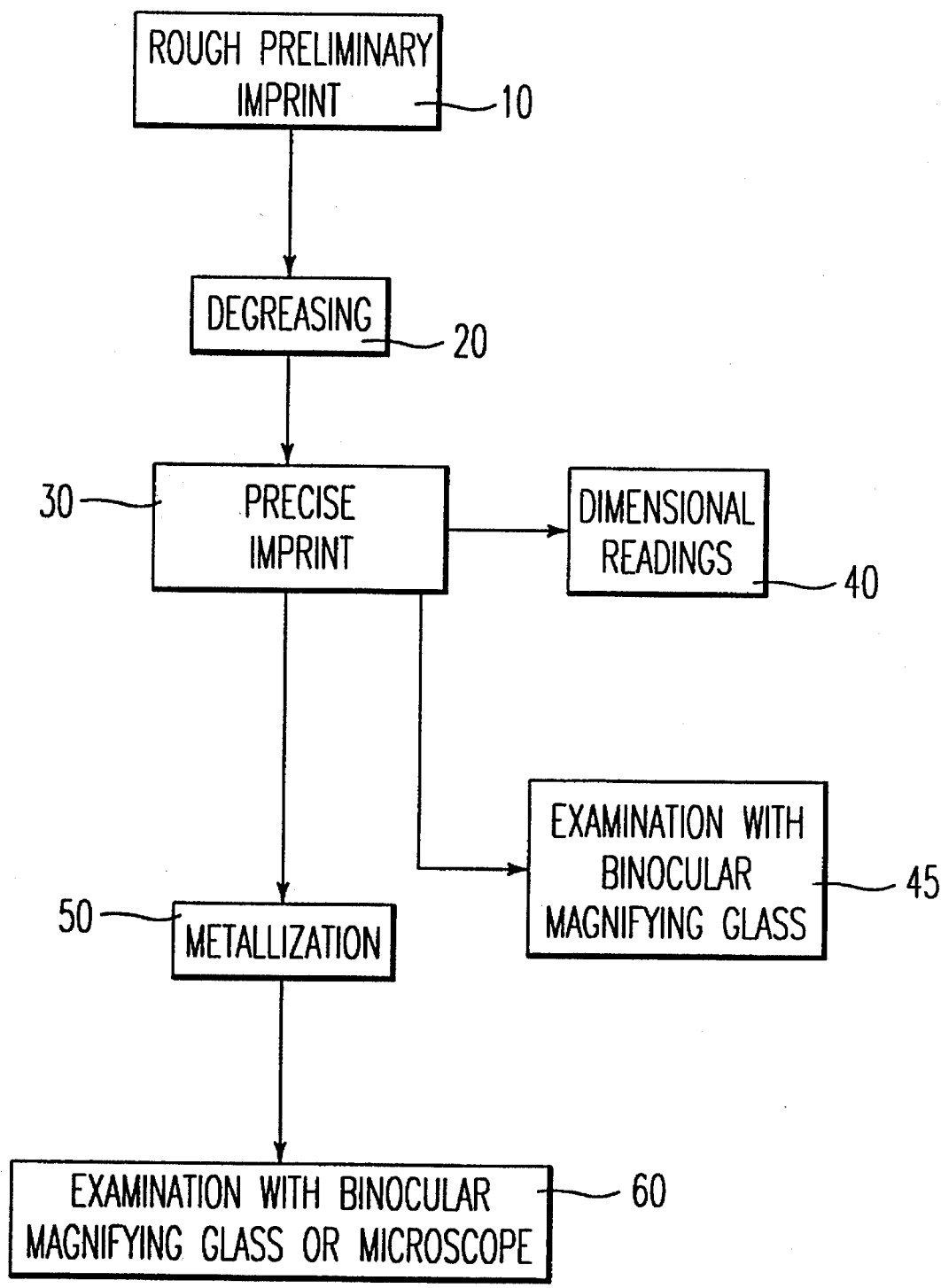
FIG. 1 is a block diagram of the stages in one embodiment of the process in accordance with the invention.

In the process represented in FIG. 1, the first stage 10 of the process consists of making a preliminary imprint of the surface to be examined by applying to the surface a first elastomeric material in paste form, the material being of medium precision so that the preliminary imprint is formed roughly. This material is held in place for the time required for it to set, so that the rough preliminary imprint effectively forms a supporting mold.

In the second stage 20, after the preliminary imprint has been removed, the surface to be reproduced is carefully degreased with pure acetone.

The next stage 30 involves making a precise imprint of the surface to be examined. To do this, an impression element is formed by casting a second elastomeric material of high precision in the supporting mold obtained in the first stage 10, the impression element is applied to the surface to be reproduced and a slight pressure exerted for a few seconds, and the impression element is then held in place for sufficient time for it to harden before being removed.

This imprint may then be used to carry out dimensional readings of the surface condition by means of, for example, a surface profilometer by laser convergence (stage 40), and/or for examination with a binocular magnifier (stage 45). The imprint may also be examined (stage 60) with a binocular magnifier, or an optical microscope, or a scanning electron microscope, after first having been metallized under vacuum (stage 50). Metallization may be carried out, for example, in an evaporator or in a cathode pulverizer, and the thickness of the deposit is of the order of a few hundredths of a micron.

By way of example, the first and second elastomeric materials may be chosen from the family of plasticizer-charged silicones. The consistency of this type of material is dependent on the amount of plasticizer added to the silicone. To obtain reproduction of details with good precision, the consistency of the material must not be too great. Thus, the first material chosen to make the preliminary imprint has a greater consistency than the second material chosen to make the final high precision imprint.

Figure 2A:
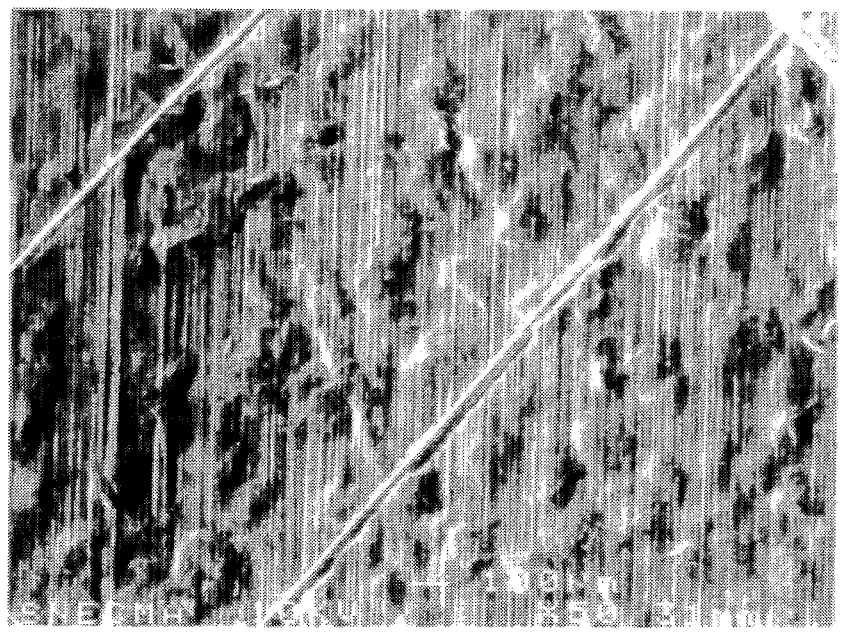
FIG. 2a is a photograph of an area of a shot blasted specimen revealing absences of coverage.
Figure 2B:
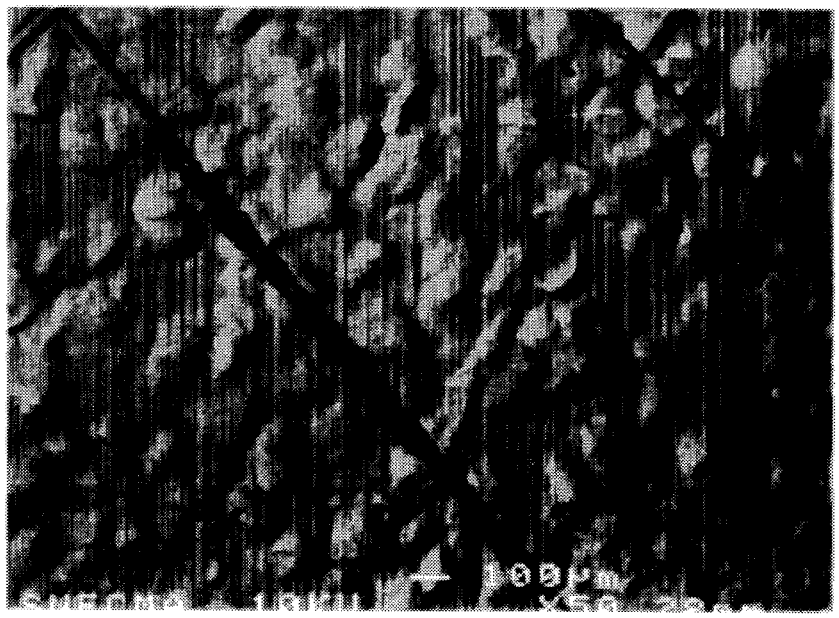
FIG. 2b is a photograph of an imprint of the same area of the specimen obtained in accordance with the invention.

FIGS. 2a and 2b show respectively a photograph of a shot blasted testpiece exhibiting covering deficiencies and a photograph of an imprint of the same testpiece. Both photographs were taken with a scanning electron microscope at a magnification of 50. the shot blasted specimen has marker lines and shows ball impacts on machining traces.

The imprint of the specimen was made using, in succession, two elastomeric materials consisting of silicone oil charged with plasticizers, these materials being obtainable under the brand name PROVIL from the BAYER company. The preliminary imprint was made using the product PROVIL P SOFT having a hardness of between 60 and 70 Shore A, and the high precision imprint was made using the product PROVIL CD M having a hardness of between 50 and 55 Shore A. The high precision imprint thus made was metallized under vacuum by depositing pure aluminium to a thickness of the order of 0.03 micron.

The images shown in FIGS. 2a and 2b are inverted relative to each other due to the fact that the effect of taking an imprint is to reverse the data of the surface from which the imprint is taken. In FIG. 2b, the electrical signal was inverted on the scanning electron microscope, so as to obtain a positive topographic view of the surface as in FIG. 2a.

The photograph of FIG. 2b taken from the imprint of the surface of the specimen is in every respect comparable with that obtained in FIG. 2a directly from the specimen.

Figure 3A:
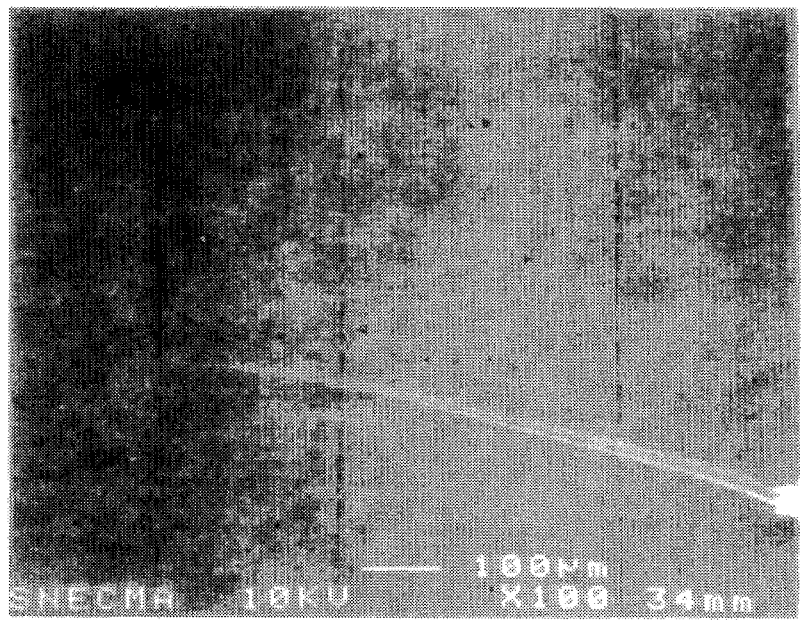
FIG. 3a is a photograph of an area of gauge block exhibiting cracks of 0.5 micron width; and, FIG. 3b is a photograph of an imprint of the same area of the gauge block obtained in accordance with the invention.
Figure 3B:

FIG. 3a is a photograph of an area of a gauge block having cracks of 0.5 micron width, and FIG. 3b is a photograph of an imprint of the same area of the gauge block.

The photographs were taken with a scanning electron microscope at a magnification of 100. The cracks present on the gauge block are the result of traction exerted on the gauge block coated on one face with a deposit of nickel/chromium to a thickness of 5 microns to the nearest 5%. The depth of the cracks is equal to the thickness of the nickel/chromium deposit. The photograph shown in FIG. 3b of the imprint of the gauge block shows the cracks with as much precision as the photograph of FIG. 3a taken directly from the gauge block.

As the cracks have a width of the order of 0.5 micron, this method therefore permits inspection of the surface condition of a mechanical part with a degree of precision at least equal to 0.5 micron.

Similarly, roughness measurements were taken from a glass gauge block having a surface condition characterized by a mean roughness of the order of 0.86 micron. The roughness measurements taken from an elastomeric imprint of the gauge block made in accordance with the invention show an arithmetic mean deviation of the order of 4% relative to the measurements taken from the gauge itself. The results thus obtained are clearly better than those obtained by known methods, such as, for example, using an imprint made with a fluid resin obtainable under the registered trade mark TECHNOVIT and used in particular in metrology for obtaining dimensional readings. Indeed, the mean deviation obtained with this type of resin is of the order of 10%.

The invention is not of course limited to the particular embodiments which have been described in detail. The imprints may be inspected with a binocular magnifying glass before and/or after metallization, or with an optical microscope or scanning electron microscope after metallization depending on the degrees performance, magnification and field depth desired.

Moreover, the metallization effected for examining the imprints need not necessarily be an aluminium deposition. Any other suitable metal deposit may be used, such as, for example, a deposit of an alloy of gold and palladium.

I claim:

1. A non-destructive process for characterizing the surface condition of a part, including the steps of:

applying a first elastomeric material in paste form to the surface to be checked and allowing said first elastomeric material to harden to obtain a supporting mold bearing a preliminary imprint of said surface;

casting a second elastomeric material in paste form into said supporting mold to form an impression element, said second elastomeric material having a mean consistency permitting the reproduction of detail with an accuracy of the order of a few tenths of a micron;

applying said impression element to said surface to be checked so as to obtain a final imprint of said surface in said impression element;

holding said impression element in place on said surface for sufficient time for said element to harden; and, removing said hardened element with said final imprint from said surface.

2. A process as claimed in claim 1, further including the step of measuring the roughness of said final imprint using a laser convergence surface profilometer.

3. A process as claimed in claim 1, further including the step of examining said final imprint using a binocular magnifying glass.

4. A process as claimed in claim 1, further including the steps of:

forming a metallic deposit having a thickness of the order of a few hundredths of a micron under vacuum on said final imprint to metallize said final imprint;

and examining said metallized final imprint using a binocular magnifying glass, an optical microscope or a scanning electron microscope.

5. A process as claimed in claim 1, wherein said first and second elastomeric materials are selected from the family of plasticizer-charged silicones.

* * * * *